United States Patent [19]

Watanabe

[11] Patent Number: 4,500,205

[45] Date of Patent: Feb. 19, 1985

[54] SPECTROPHOTOMETER

[75] Inventor: Shinichiro Watanabe, Tokyo, Japan

[73] Assignee: Japan Spectroscopic Co., Ltd., Hachioji, Japan

[21] Appl. No.: 465,683

[22] Filed: Feb. 10, 1983

[30] Foreign Application Priority Data

Feb. 15, 1982 [JP] Japan .................................. 57-23248

[51] Int. Cl.³ .............................................. G01J 3/42
[52] U.S. Cl. .................................................. 356/325
[58] Field of Search ................ 356/319, 323, 324, 325

[56] References Cited

U.S. PATENT DOCUMENTS 3,813,168  5/1974  Honkawa ......................... 356/325 X
3,972,617  8/1976  Shibata et al. .................. 356/325 X Primary Examiner—F. L. Evans
Attorney, Agent, or Firm—Wenderoth, Lind & Ponack

[57] ABSTRACT

In a spectrophotometer of double beam type comprising a radiation source, reference and sample cells, a photo detector, and beam path switching means, a current-voltage converting amplifier and a logarithmic amplifier in parallel connection are connected to the photo detector. In measuring the transmittance of a sample material in the sample cell, an output of the detector responding to a sample cell transmitted beam is directly supplied to the logarithmic amplifier without undergoing current-voltage conversion while an output of the detector responding to a reference cell transmitted beam is supplied to the current-voltage converting amplifier without undergoing logarithmic amplification.

7 Claims, 9 Drawing Figures

SPECTROPHOTOMETER

BACKGROUND OF THE INVENTION

This invention relates to spectrophotometers of double beam type, and more particularly, to spectrophotometers of the type wherein an output resulting from the detection of a radiation beam transmitted through a sample material to be analyzed is logarithmically amplified to provide a direct logarithmic representation of the spectral transmittance of the sample material.

As is well known in the art, in the spectrophotometer of double beam type, monochromatic radiation of varying wavelengths is alternately directed to a reference cell and a sample cell containing a sample material to be analyzed to form reference and sample beams which are received by a radiation detector which in turn, produces corresponding electrical outputs, the detector is controlled in a feedback manner such that an output of the detector which responds to the reference beam may be equal to a reference voltage, an output of the detector responding to the sample beam is compared with that of the detector responding to the reference beam at each wavelength, and the ratio of these outputs is derived as the transmittance of the sample.

Among such conventional spectrophotometers, are known spectrophotometers of so-called dynode feedback system using a photodetector in the form of a photomultiplier whose gain is automatically controlled such that outputs of the multiplier which responds to radiation transmitted through a reference cell may be constant at all wavelengths at which measurements are made. One example of these prior art spectrophotometers is shown in FIG. 7.

Referring to FIG. 7, there is illustrated at 1 a main section of a prior art spectrophotometer which includes a radiation source 2 capable of emitting monochromatic radiation of varying wavelengths, for example, a monochromator, a sample chamber or cell 3 containing a sample material to be analyzed, a reference chamber or cell 4 to be described later, a photo detector in the form of a photomultiplier 5, and beam path swithing means 6 for causing monochromatic radiation from the source 2 to alternately enter the sample cell 3 and the reference cell 4 to form sample and reference beams and directing in synchronism the sample and reference beams from the sample and reference cells 3 and 4 alternately to the photomultiplier 5. The reference cell 4 is used in the state that its transmittance is substantially 100% and it shows no characteristic spectral response, that is, in an empty state (an empty cell is placed in the beam path) or in the state that the cell is charged with a standard material having flat spectral response and high transparency. The beam path switching means 6 includes an inlet beam path switching device 7 called a sector adapted to be rotated by means of a motor (not shown) so as to alternately direct the radiation from the source 2 to the sample cell 3 and the reference cell 4 to form sample and reference beams, and an outlet beam path switching device 8 adapted to be rotated in synchronism with the inlet beam path switching device 7 so as to alternately direct the sample and reference beams to the photomultiplier 5. The beam paths extending from the inlet beam path switching device 7 to the outlet beam path switching device 8 through the sample and reference cells 3 and 4 are simply referred to as "sample path" and "reference path", respectively, in this specification. An output of the photomultiplier 5 is supplied to a sample/hold circuit 9 and an error control circuit 10 through an amplifier 11 as will be described in more detail.

The photomultiplier 5 or the amplifier 11 produces output signals S as shown in FIG. 8(A). In the diagram of FIG. 8(A), a represents an impulse corresponding to the reference beam, i.e. beam transmitted through the reference cell 4, and b represents an impulse corresponding to the sample beam, i.e. beam transmitted through the sample cell 3. A low level portion c between these impulses a and b corresponds to background radiation during beam path switching including dark current. The sample/hold circuit 9 is designed to effect sampling in synchronism with a timing pulse TA developed in the duration when the beam path switching means 6 is switched to provide the sample path, that is, the duration of an impulse b as shown in FIG. 8(B). The sample/hold circuit 9 thus produces an output corresponding to the level of an impulse b among output signals S of the amplifier 11, that is, an output correspoding to the intensity of the same beam. Further, the error control circuit 10 functions to derive a signal corresponding to the intensity of the reference beam among output signals S of the amplifier 11, compare it with a reference voltage to determine the difference between them, and control the sensitivity of the photomultiplier 5 in accordance with said difference in a feedback manner such that the impulses a representative of the reference beam intensity among output signals S of the amplifier 11 may be kept at a constant level. In the illustrated example, the error control circuit 10 consists of a circuit 10A for generating a reference voltage and a synchronization error integrator 10B adapted to operate in synchronism with a timing pulse TB developed in the duration when the beam path switching means 6 is switched to provide the reference path, that is, the duration of an impulse a as shown in FIG. 8(C), for reading out the level of the impulse a and integrating the difference between said level and the reference voltage. Since the synchronization error integrator 10B is electrically connected to a high voltage source 12 which drives the photomultiplier 5, the output voltage of the source 12 is controlled by the output of the integrator 10B.

Since the detection system of the spectrophotometer shown in FIG. 7 is controlled such that impulses a among output signals S of the amplifier 11, that is, outputs of the detector which responds to the sample beam are kept at a constant level at all wavelengths, the output of the sample/hold circuit 9 not only corresponds to the intensity of the sample beam, but also directly represents the ratio of the intensity of the sample beam to the intensity of the reference beam at each wavelength, that is, the transmittance of the sample material itself at each wavelength.

The spectral transmittance of a sample material may be represented in two modes, the so-called percentage representation in which the ratio of the intensity of a sample beam to a reference beam is represented in percent, and the so-called logarithmic representation in which the intensity of a sample beam is converted into a logarithmic value and the ratio of the resulting logarithmic value to the intensity of a reference beam is represented. The percentage representation has the advantage that the transmittance of a sample is directly read out. The logarithmic representation is desirable in some cases. That is, where the spectral transmittance of a sample material is considerably low, the logarithmic representation provides more definite recognition of a difference in transmittance.

Radiation detectors, for example, photomultipliers used in conventional spectrophotometers are of current output type whose output current varies with the intensity of radiation. To provide for logarithmic representation in a spectrophotometer using such a detector, it is a common practice in the art to use a current-voltage converting amplifier in combination with a logarithmic amplifier. More specifically, as shown in FIG. 9, a radiation detector in the form of a photomultiplier 5 is series connected to a current-voltage converting amplifier or pre-amplifier 11A and a logarithmic amplifier 11B. A photo current of the photomultiplier 5 is converted and amplified by the pre-amplifier 11A into a voltage which is logarithmically amplified by means of the logarithmic amplifier 1OB. However, such prior art logarithmic representation systems suffer from the drawbacks that noises, drift, offset voltage and other factors induced in the pre-amplifier 11A cause the logarithmically converted data output to contain noise or deleteriously affect the linearity of them. Their influence becomes significant when the radiation transmittance of a sample is low, or an output current of the photo detector is of a small magnitude, resulting in an increased error in measurement. On the contrary, when the sample transmitted beam has a great intensity, the corresponding output of the photo detector will probably be saturated in the pre-amplifier, failing to fully utilize the dynamic range of the photo detector and logarithmic amplifier. It is thus difficult to expand the dynamic range of the entire system to increase measurement accuracy.

To obviate these problems, a spectrophotometer has been proposed in which a photo current of the photo detector is directly supplied to a logarithmic amplifier. However, this type of spectrophotometer is limited to the single monochromatic system which detects only the intensity of a radiation beam transmitted through a sample material and is believed to be applied to the double beam type system only with difficulty. If the above-mentioned logarithmic conversion system is applied without any change to the double beam system in which the detector is controlled in a fedback manner such that an output of the detector responding to a reference beam is equal to a reference voltage, then the detector output responding to the reference beam is also subjected to logarithmic conversion, resulting in the loss of linearity of the detector output responding to the reference beam. This leads to the problem that processing such as correction of the detector output responding to the reference beam and the reference voltage becomes complicated. The double beam system has the advantage that it can cancell the influence of background radiation by subtracting a detector output developed in the duration when the beam path is being switched from one cell to the other cell in the spectrophotometer main section, that is, an output of the detector responding to background radiation (including dark current in the circuit or elements) from an output of the detector which responds to a sample or reference beam, thereby ensuring more accurate analysis. However, the logarithmic convertion of a background radiation output requires more complicated processing.

It is, therefore, an object of the present invention to provide a novel and improved spectrophotometer of the double beam type to which the logarithmic conversion of a detector output is performed into provide a logarithmic representation of the spectral transmittance of a sample material in such a manner that logarithmically converted output data undergo minimal noise influence and have good linearity, and the dynamic range of the measuring system is expanded, thereby significantly improving measurement accuracy over the prior art technique.

SUMMARY OF THE INVENTION

The present invention provides a spectrophotometer of the type comprising a radiation source, a reference cell, a sample cell, a radiation detector which produces an electrical output, and beam path switching means for directing monochromatic radiation of varying wavelengths from the source alternately to the reference and sample cells to form reference and sample beams and directing in synchronism the reference and sample beams to said detector, wherein an output of said detector which responds to the reference beam is fed back to said detector such that said output may be equal to a reference voltage upon measurement of a sample material in said sample cell at all wavelengths whereby an output of said detector which responds to the sample beam represents the transmittance of the sample for each wavelength. The spectrophotometer of the invention further comprises a current-voltage converting amplifier connected to the output terminal of said detector, a logarithmic amplifier connected to the output terminal of said detector, and synchronization switching means for alternately rendering said current-voltage converting amplifier and said logarithmic amplifier operative in synchronism with the operation of said beam path switching means, whereby selection is made by means of said synchronization switching means in synchronism with the operation of said beam path switching means between at least two states, a first state where an output of said detector is directly fed to said logarithmic amplifier without passing said current-voltage converting amplifier and a second state where an output of said detector is directly fed to said current-voltage converting amplifier without passing the logarithmic amplifier.

BRIEF DESCRIPTION OF THE DRAWINGS

The invention will be more fully understood by reading the following description of preferred embodiments when taken in conjunction with the accompanying drawings, in which.

DETAILED DESCRIPTION OF THE INVENTION

Figure 1:
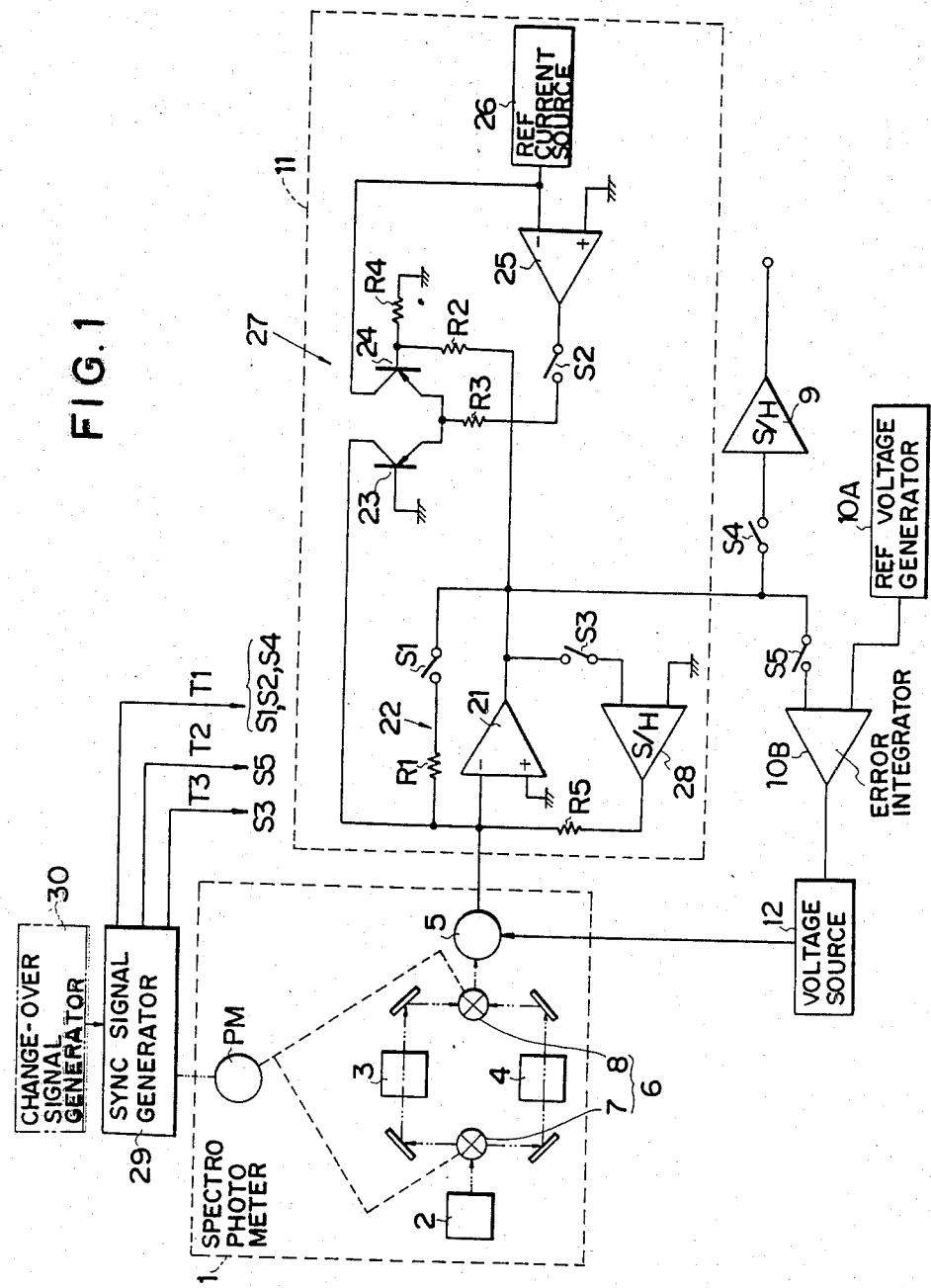
FIG. 1 is a block diagram of one embodiment of the spectrophotometer of the invention.
Figure 7:
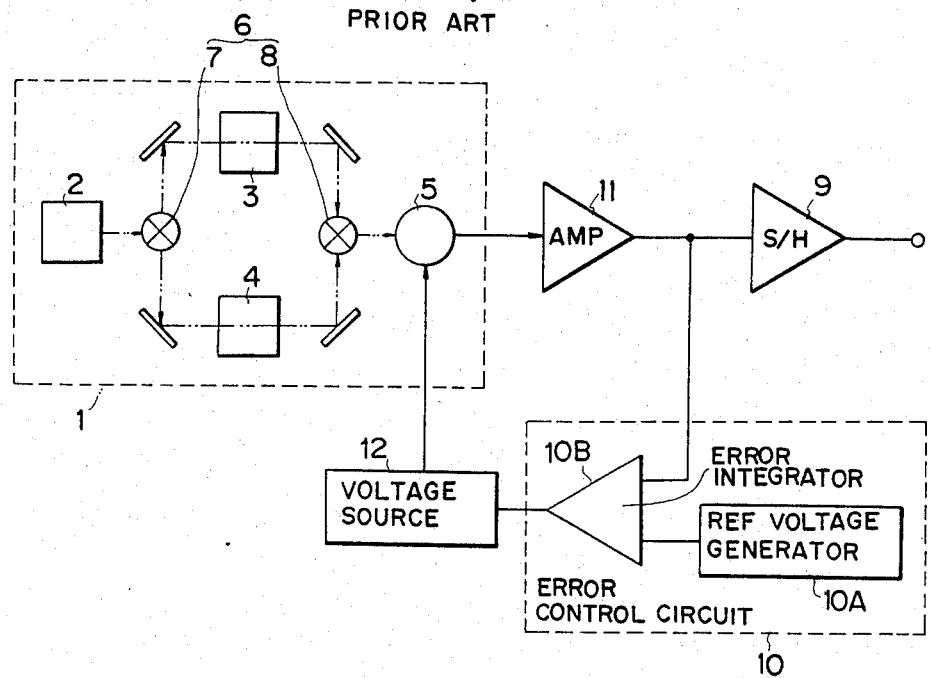
FIG. 7 is a block diagram of one example of the prior art spectrophotometer.
Figure 8:
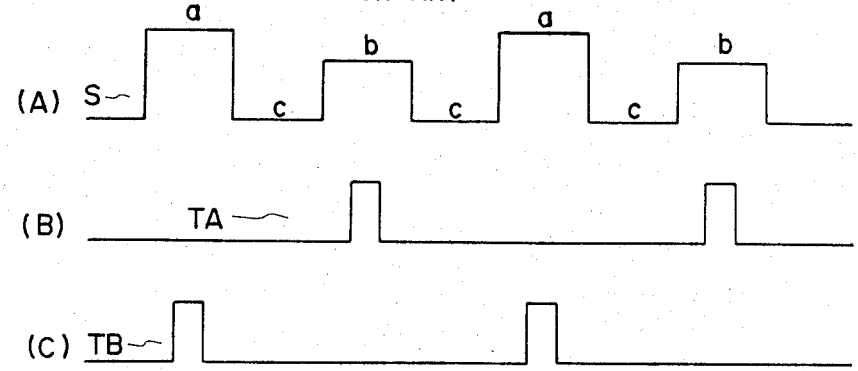
FIG. 8 is a time chart showing waveforms of signals appearing at various points in the spectrophotometer shown in FIG. 7.
Figure 9:
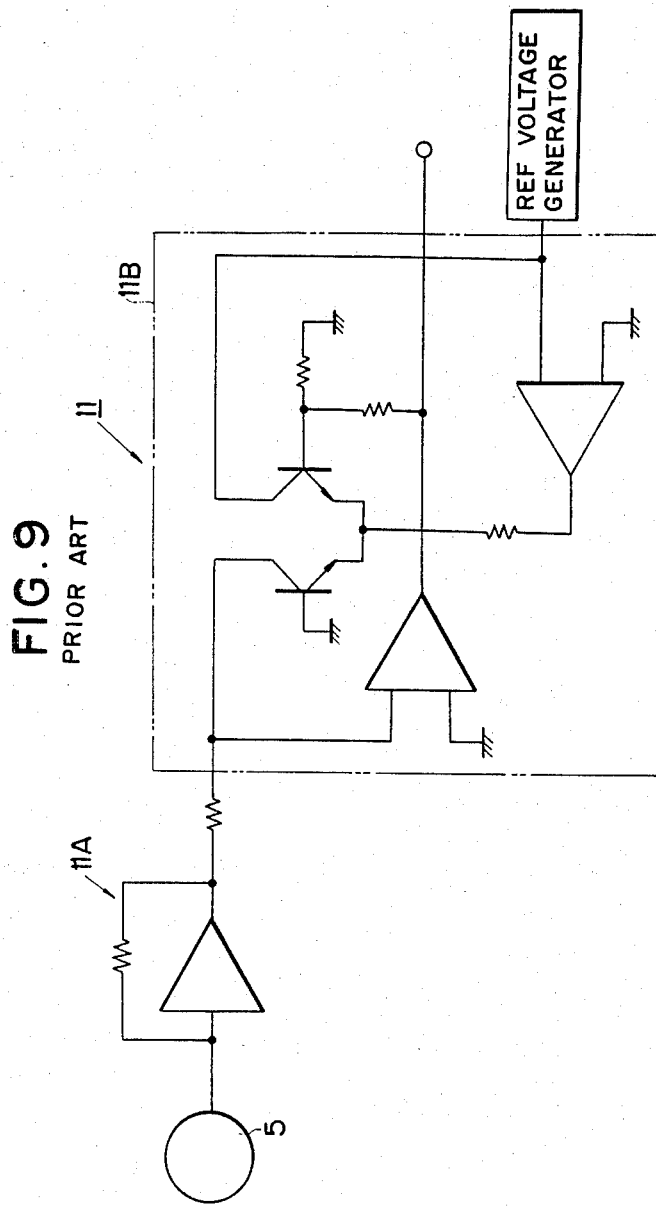
FIG. 9 is a diagram showing a circuit used in the prior art spectrophotometer for logarighmic representation.

Referring to FIG. 1, there is shown one embodiment of the spectrophotometer of double beam type according to the present invention. Since a main section of the spectrophotometer shown in FIG. 1 is essentially the same as that of the prior art spectrophotometer shown in FIG. 7, and like numerals designate like parts in the figures, the organization and operation of the main section will be understood without further explanation. A portion 11 bounded by broken lines in rectangular form is an essential portion constituting the invention and corresponds to the amplifier 11 in FIG. 7.

The output terminal of the photomultiplier 5 is electrically connected to a negative input terminal of a first operational amplifier 21 which has a positive terminal grounded and an output terminal connected in a feedback manner to the negative input terminal by way of a series connection of a first switch S1 and a resistor R1. With the first switch S1 closed, the first operational amplifier 21 operates in a negative feedback mode, providing amplification function. The first operational amplifier 21 and the resistor R1 form a current-voltage converting amplifier 22.

Further, the negative input terminal of the first operational amplifier 21 or the output terminal of the photomultiplier 5 is electrically connected to the collector of a transistor 23 serving as a first non-linear or logarithmic element, while the output terminal of the first operational amplifier 21 is electrically connected to the base of another transistor 24 serving as a second non-linear or logarithmic element by way of a resistor R2. The transistors 23 and 24 have commonly connected emitters, and the output terminal of a second operational amplifier 25 is connected to this common connection by way of a second switch S2 and a resistor R3. The second operational amplifier 25 has a positive input terminal grounded and a negative input terminal connected to both a reference current source 26 and the collector of the second transistor 24. The first transistor 23 has a gounded base and the base of the second transistor 24 is grounded via a resistor R4. The transistors 23 and 24, reference voltage source 26, and first and second operational amplifier 21 and 25 form a logarithmic amplifier 27. More specifically, with the second switch S2 closed and the first switch S1 opened, the circuit consisting essentially of the transistors 23 and 24, reference current source 26, and first and second operational amplifiers 21, and 25 functions to logarithmically amplify an output of the photomultiplier 5. Since the first switch S1 is opened in this condition, the first operational amplifier 21 does not function as the current-voltage converting amplifier 22. In this manner, the first operational amplifier 21 is a common element to the current-voltage converting amplifier 22 and the logarithmic amplifier 27 in the illustrated embodiment.

In the circuit illustrated in FIG. 1, the output terminal of the first operational amplifier 21 is connected to a second sample/hold circuit 28 through a third switch S3. The second sample/hold circuit 28 has an output terminal connected to the negative input terminal of the first operational amplifier 21 through a resistor R5. With this arrangement, the first operational amplifier 21 carries out subtractive operation between its output at a time just when the third switch S3 is closed and its input applied immediately thereafter.

The common connection between the output terminals of the current-voltage converting amplifier 22 and the logarithmic amplifier 27, i.e., the output terminal of the first operational amplifier 21 and the resistor R2 of the logarithmic amplifier 27 is connected to a first sample/hold circuit 9 through a fourth switch S4 and to a synchronization error integrator circuit 1OB through a fifth switch S5. The first sample/hold circuit 9 is the same as that shown in FIG. 7 and its outputs are read out as analytical data. The analytical data may be processed in a well-known manner for record or display purpose. The integrator circuit 1OB is also the same as that shown in FIG. 7. The voltage applied from a high voltage source 12 to the photomultiplier 5 is controlled such that the voltage applied to the integrator circuit 1OB through the fifth switch S5 may be equal to a reference voltage. It is to be noted that the reference voltage used herein is not necessarily a fixed voltage as will be described later. More particularly, prior to an actual measurement stage of analyzing a sample material, preparatory scanning may be carried out including setting the sample and reference cells 3 and 4 to a substantially 100% transmittance state, scanning the sample and reference cells 3 and 4 with radiation of each wavelength in this state, and storing an output of the detector which responds to a reference beam with the sample cell 3 set to a substantially 1OO% transmittance state. Then, the stored output may be read out and used as a reference voltage upon measurement of a sample material at each wavelength. In this case, if the sample path and the reference path in the spectrophotometer main section 1 are different in spectral response, then said reference voltage varies with wavelength in accordance with the spectral response difference.

Figure 2:
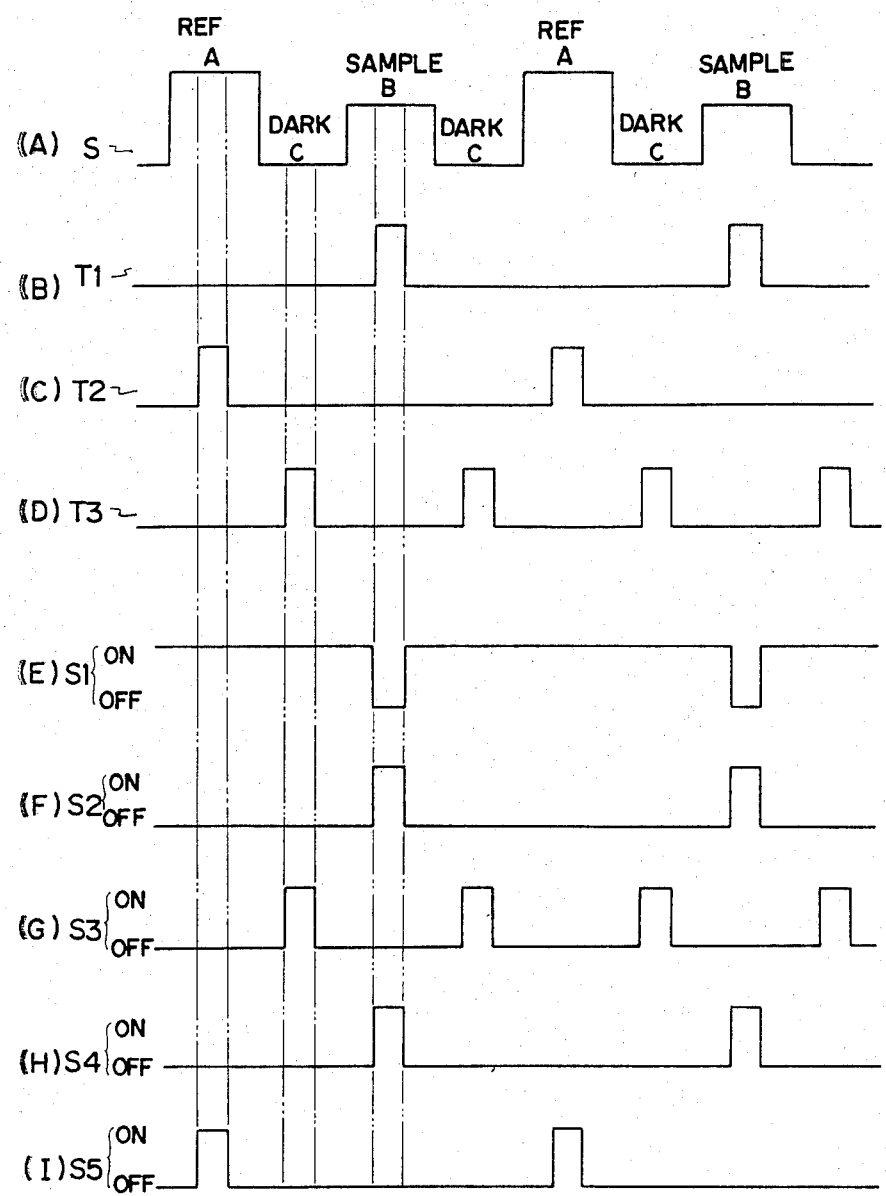
FIG. 2 is a time chart showing waveforms of signals appearing at various points in the apparatus shown in FIG. 1.

The above-mentioned switches S1, S2, S3, S4 and S5 each consist of a non-contact switch generally in the form of a field effect transistor and are opened and closed in a controlled manner by timing signals T1, T2 and T3 from a sync signal generating circuit 29. The switches S1, S2 and S4 are controlled by a first timing signal T1, the third switch S3 is controlled by a third timing signal T3, and the fifth switch S5 is controlled by a second timing signal T2. The sync signal generating circuit 29 is designed such that it may generate the first, second and third timing signals T1, T2 and T3 in response to signals from the beam path switching devices 7 and 8 of the beam path switching means 6 or a pulse motor PM for driving them. By referring to the time chart of FIG. 2 showing waveforms at various points in the circuit of FIG. 1, it will be described how the timing signals T1, T2, and T3 synchronize the operation of the switches S1 to S5 and how the whole system operates accordingly.

The waveform of an output signal S produced by the photomultiplier 5 is shown in FIG. 2(A). In the diagram of FIG. 2(A), impulses A are outputs of the detector which responds to the reference beam, i.e. beam transmitted through the reference cell 4 (to be referred to as "reference output", hereinafter), impulses B are outputs of the detector which responds to the sample beam, i.e. beam transmitted through the sample cell 3 (to be referred to as "sample output", hereinafter), and low level portions C between the adjoining impulses A and B correspond to background radiation during beam path switching including dark current. FIGS. 2(B), 2(C) and 2(D) illustrate the timing signals T1, T2 and T3 in normal measurement of a sample material to be analyzed, respectively. FIGS. 2(E) to 2(I) illustrate the operation of the switches S1 to S5, respectively.

In normal measurement of a sample material, the first timing signal T1 is a pulse developed just within the duration when the beam is switched to follow the sample path, that is, the duration of a sample output impulse B, the second timing signal T2 is a pulse developed just within the duration when the beam is switched to follow the reference path, that is, the duration of a reference output impulse A, and the third timing signal T3 is a pulse developed just within the duration C of background radiation. The first switch S1 is opened only for the duration of a first timing signal T1, the second and fourth switches S2 and S4 are closed only for the duration of a first timing signal T1, the third switch S3 is closed only for the duration of a third timing signal T3, and the fifth switch S5 is closed only for the duration of a second timing signal T2.

Consequently, in the duration of a reference output impulse A, closing of the first switch S1 and opening of the second switch S2 render the logarithmic amplifier 27 inoperative and the current-voltage converting amplifier 22 operative because of application of negative feedback to the first operational amplifier 21. In this condition, an output current of the photomultiplier 5 is linearly amplified after conversion into a voltage by the current-voltage converting amplifier 22 without passing the logarithmic amplifier. Since the fifth switch S5 is closed in this duration, the amplified output is supplied from the amplifier to the synchronization error integrator circuit 10B through said switch S5. As a result, the sensitivity of the photomultiplier 5 is controlled in a feedback manner such that the amplified outputs of reference output impulses A may be equal to the reference voltage at any wavelengths. Since the fourth switch S4 is open in this duration, the amplified outputs of reference output impulses A are not sent to the first sample/hold circuit 9 or outside the circuit as analytical data.

On the other hand, in the duration of a sample output impulse B, opening of the first switch S1 and closing of the second switch S2 render the current-voltage converting amplifier 22 inoperative because of cancelled negative feedback to the first operational amplifier 21 and the logarithmic amplifier 27 operative. In this condition, an output current (or sample output) of the photomultiplier 5 is directly logarithmically amplified by the logarithmic amplifier 27 without passing the current-voltage converting amplifier. Since the fourth switch S4 is closed in this duration, the logarithmically amplified outputs corresponding to sample outputs are sent to the first sample/hold circuit 9 and read out of the circuit as sequential analytical data. Since the sensitivity of the photomultiplier 5 is feedback controlled such that the amplified outputs corresponding to reference output impulses A may be equal to the reference voltage at any wavelengths, the output of the first sample/hold circuit 9 corresponds to the ratio of the logarithmic value of a sample output to the reference voltage. If the reference voltage is a fixed voltage, then the output of the first sample/hold circuit 9 always represents the ratio of the logarithmic value of a sample output to the reference voltage at all wavelengths. If, prior to actual measurement of a sample material, both the sample and reference cells 3 and 4 are set to a substantially 100% transmittance state and scanned with radiation of varying wavelengths in this state, an amplified detector output corresponding to a reference beam with the sample cell 3 set to a substantially 100% transmittance is stored, and the signal stored in the preparatory scanning stage is read out and used as a reference voltage in the subsequent measurement of a sample material, then an output of the first sample/hold circuit 9 represents at each wavelength the ratio of the logarithmic value of a detected output of the beam which has transmitted a sample material to the logarithmic value of a detected output of the beam which has transmitted through a substantially 100% transmittance sample cell 3. Since the fifth switch S5 is opened in the duration of a sample output impulse B, an output of the logarithmic amplifier 27 is not sent to the synchronization error integrator circuit 10B.

Further, in the duration C corresponding to background radiation, closing of the third switch S3 upon receipt of a third timing signal T3 causes the second sample/hold circuit 28 to hold the level of an output corresponding to background radiation. Then, the first operational amplifier 21 operates to subtract the background radiation level from both the levels of reference and sample ouput impulses A and B, providing accurate amplified outputs free of the influence of background radiation.

As described above, in providing a logarithmic representation of measured data using the circuit of FIG. 1, the sample output is directly logarithmically converted and amplified without undergoing current-voltage conversion, whereas the reference output and the background output are current-voltage converted and amplified without undergoing logarithmic conversion. It will also be understood that the first and second switches S1 and S2 constitute the aforementioned synchronization switching means.

The foregoing description refers to the logarithmic representation of measured data although percentage representation may also be offered by the circuit of FIG. 1. If the first switch S1 is always closed and the second switch S2 is always opened, then the logarithmic amplifier 27 is always inoperative and the current-voltage converting amplifier 22 is always operative. Consequently, sample outputs are derived without undergoing logarithmic conversion and the resulting read-out data represent the transmittance of a sample material in percentage. It is to be noted that the third, fourth and fifth switches S3, S4 and S5 are controlled in the same manner as in the logarithmic representation mode. Such control may be achieved by sending a first timing signal T1 to only the fourth switch S4 and not to the first and second switches S1 and S2, and sending second and third timing signals T2 and T3 to the fifth and third switches S5 and S3, respectively, as in the logarithmic representation mode. The circuit of FIG. 1 may be changed between the logarithmic and percentage representation modes by inserting a gate circuit which is controllable by a representation mode signal into the route along which the first timing signal T1 is supplied to the first and second switches S1 and S2. Of course, this representation mode signal may be afforded by providing a manual switch for the operator.

Although the foregoing description refers only to the measurement of a sample material, in some cases, a preparatory scanning stage is provided prior to the sample analyzing or measuring stage. In the preparatory scanning stage, both the sample and reference cells 3 and 4 are set to a substantially 100% transmittance state and scanned with radiation of varying wavelengths. If the sample and reference paths are not precisely identical in spectral response due to fogging or staining of mirrors in the spectrophotometer main section, then only controlling the amplified level of a reference output so as to be equal to a fixed reference voltage in the measurement of a sample material is insufficient for the detected output in the measurement of the sample material to correctly represent the transmittance of the sample material, resulting in an error at those wavelengths at which the sample and reference paths have different spectral response. To overcome this problem, preparatory scanning may desirably be carried out at each wavelength prior to the actual sample measurement.

The preparatory scanning will be described in more detail. A block 30 bounded by dot-and-dash lines in FIG. 1 is preparatory scanning/measurement scanning change-over signal generating means for changing the timing of generation of timing signals by the sync signal generating circuit 29 between the preparatory and actual measurement scanning stages. The change-over means 30 may be actuated manually by the operator's switching-on or automatically in accordance with the preset program. In response to such switching by the operator or program, the change-over means 30 produces either a signal instructing preparatory scanning or another signal instructing actual measurement.

Figure 3:
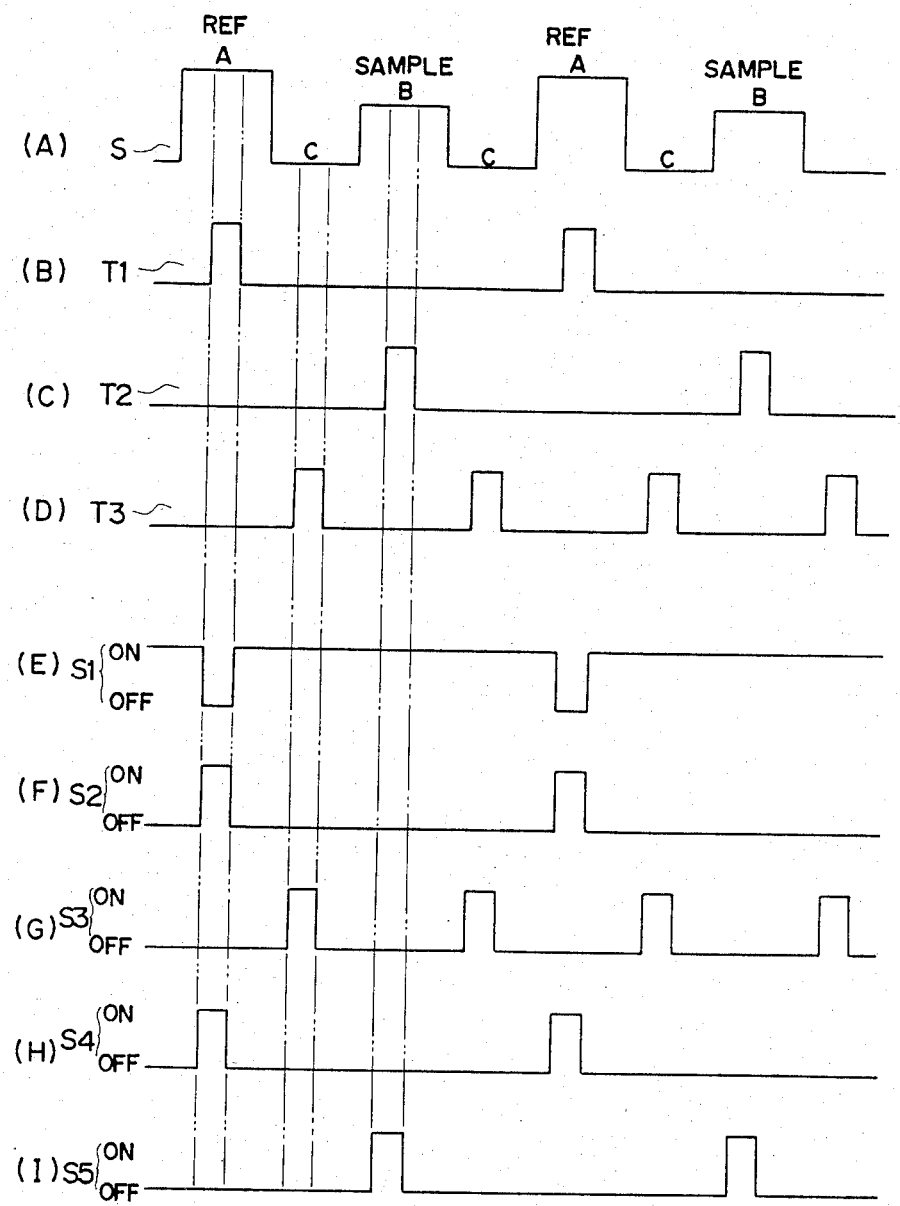
FIG. 3 is a time chart similar to FIG. 2, but the apparatus being operated in a preparatory scanning stage.

In the preparatory scanning stage prior to actual measurement of a sample material to be analyzed, the sample cell 3 is set to a substantially 100% transmittance state showing substantially no characteristic spectral response (that is, the sample cell 3 is empty or filled with a standard material having substantially no characteristic spectral response and high transparency, for example). In this state, the sample cell 3 and the reference cell 4 are alternately scanned with radiation at each wavelength in the range over which measurements of a sample material are to be made. It is a matter of course that the reference cell 4 is also set to the same state as the sample cell 3, that is, a substantially 100% transmittance state in this preparatory scanning stage. The waveforms of the timing signals T1, T2 and T3 and the corresponding operation of the switches S1 to S5 observed in the preparatory scanning prior to the actual sample measurement in the logarithmic representation mode are illustrated in FIG. 3 in conjunction with the output waveforms of the photomultiplier 5.

The first timing signal T1 shown in FIG. 3(B) is a pulse developed just within the duration of a reference output impulse A, and the second timing signal T2 in FIG. 3(C) is a pulse developed just within the duration of a sample output impulse B. That is, the first and second timing signals T1 and T2 are generated opposite to those in the sample measurement stage as shown in FIG. 2. The third timing signal T3 shown in FIG. 3(D) corresponds to background radiation as in the sample measurement stage. With these timing signals, the first and fifth switches S1 and S5 are opened and the second and fourth switches S2 and S4 are closed in the duration of a reference output impulse A. On the contrary, the first and fifth switches S1 and S5 are closed and the second and fourth switches S2 and S4 are opened in the duration of a sample output impulse B. As opposed to the above-mentioned sample measurement stage, a sample output in this case is current-voltage converted and amplified to the synchronization error integrator circuit 10B without undergoing logarithmic amplification. Feedback control is performed such that the amplified level of a sample output may be equal to the reference voltage (which is generally a fixed voltage as opposed to the sample measurement stage) and hence, a fixed voltage. On the other hand, a reference output is directly logarithmically amplified without undergoing current-voltage conversion and then derived from the first sample/hold circuit 9. The output of the first sample/hold circuit 9 resulting from logarithmic amplification of a reference output is then converted by an analog/digital converter (not shown) into a digital signal, which is stored in a computer (not shown).

When the sample and reference paths in the spectrophotometer main section have different spectral response due to fogging or staining of mirrors or the like, the level of reference output impulses A developed in the preparatory scanning is not consistent and varies with wavelength in accordance with the spectral response difference. The logarithmically amplified values of reference outputs varying with wavelength are derived from the first sample/hold circuit 9 and stored in the computer. In the subsequent sample measurement stage, a signal representative of the logarithmically amplified reference output varying with wavelength is read out for each wavelength and supplied to the reference voltage generating circuit 10A. As a result, the logarithmically amplified reference output stored in the preparatory scanning stage or the corresponding voltage is supplied to the synchronization error integrator circuit 10B as a reference voltage for each wavelength. It is to be noted that the sample analyzing procedure following the preparatory scanning stage is the same as described in connection with FIG. 2.

As described above, in the preparatory scanning stage, the sample cell 3 is set to a substantially spectral response-free state (that is, a state offering a substantially 100% transmittance at all wavelengths), sample outputs are made consistent in this state, and the corresponding reference outputs, that is, the logarithmically amplified values of detector outputs responding to reference beams which vary with wavelength in accordance with the spectral response difference between the sample and reference paths in the spectrophotometer main section are stored in the computer. In the subsequent sample measurement, for each wavelength, the logarithmically amplified reference output stored is read out and used as a reference voltage with or without further amplification to which a reference output developed in the sample measurement stage is controlled to be equal. Consequently, a reference output developed in the sample measurement stage corresponds to the logarithmically amplified value of a sample output level with the sample cell 3 to a substantially 100% transmittance state at any wavelength. Then, an output (sample output) of the first sample/hold circuit 9 always correctly represents the logarithmic transmittance of the sample material irrespective of the difference in spectral response between the sample and reference paths in the spectrophotometer main section.

Figure 4:
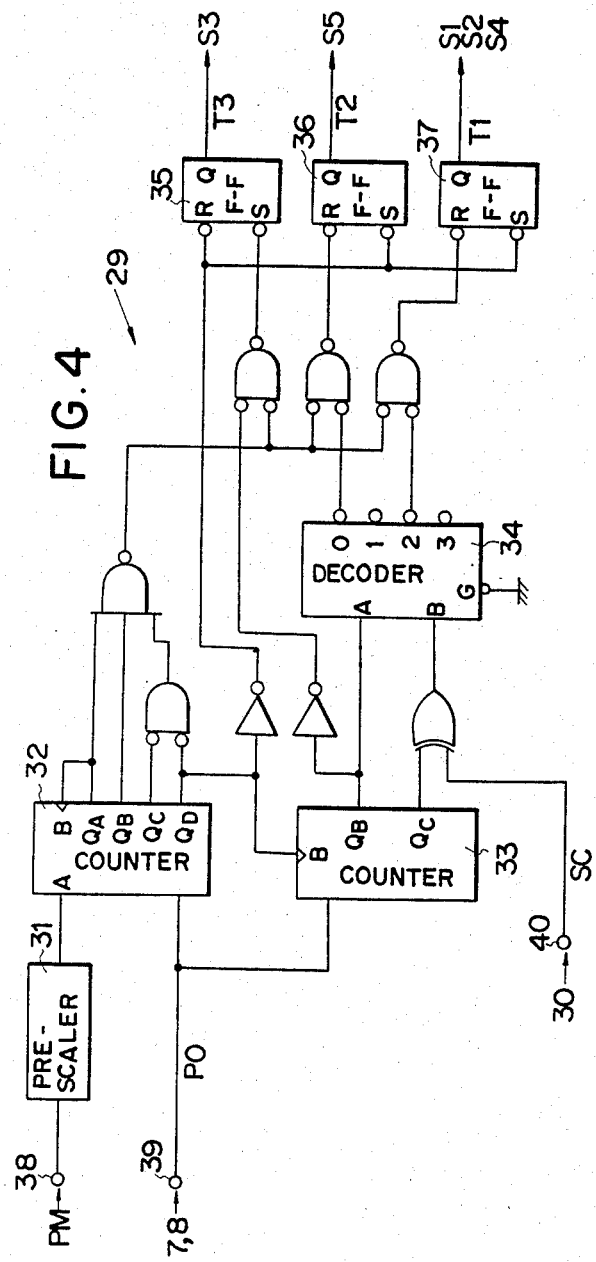
FIG. 4 is a block diagram of one example of a sync signal generating circuit used in the spectrophotometer of the invention.

FIG. 4 illustrates an example of the sync signal generating circuit 29. As seen from FIG. 4, the sync signal generating circuit 29 is composed of a pre-scaler 31, counters 32 and 33, a decoder 34, RS flip-flops 35, 36 and 37, and the like. The circuit 29 has a first input terminal 38 which receives a pulse from the pulse motor PM driving the beam path switching means 6, a second input terminal 39 which receives a sync signal PO from the beam path switching device 7 or 8 of the beam path switching means 6, that is, a pulse signal developed at the same period as the beam path switching, and a third input terminal 40 which receives a change-over signal SC from the preparatory scanning/measurement scanning change-over signal generating circuit 30. The flip-flops 35, 36 and 37 constitute outputs of this circuit 29. The flip-flop 35 develops third timing signals T3, the flip-flop 36 develops second timing signals T2, and the flip-flop 37 develops first timing signals T1.

Figure 5:
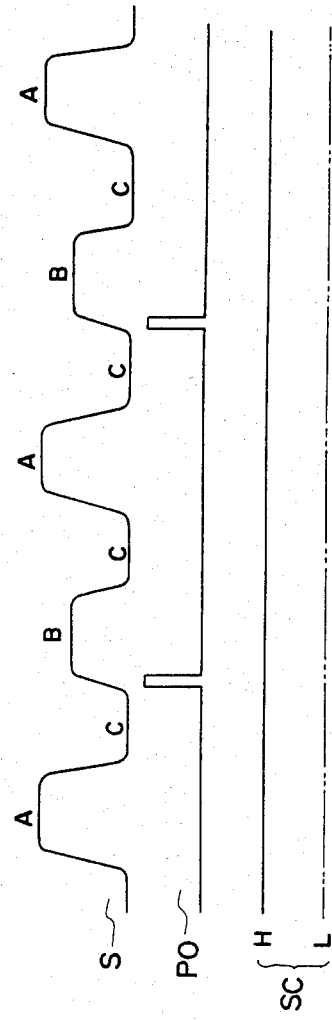
FIG. 5 is a time chart showing waveforms of signals appearing at various points in the circuit shown in FIG. 4.

The input signal OP and SC of the sync signal generating circuit 29 of FIG. 4 are shown in FIG. 5 together with the output signal S of the photomultiplier 5. The change-over signal SC is at a high level H during the preparatory scanning and at a low level L during the sample measurement, and the timing of generating the first and second timing signals T1 and T2 is determined by the level of the change-over signal SC. In order to avoid the influence of fluctuating or rounded rise and fall of reference and sample output impulses appearing at output signals S of the photomultiplier 5, the sync signal generating circuit 29 is designed such that each of the timing signals T1, T2 and T3 may be developed in a central flat portion of the reference output duration, sample output duration and background radiation duration, respectively.

Figure 6:
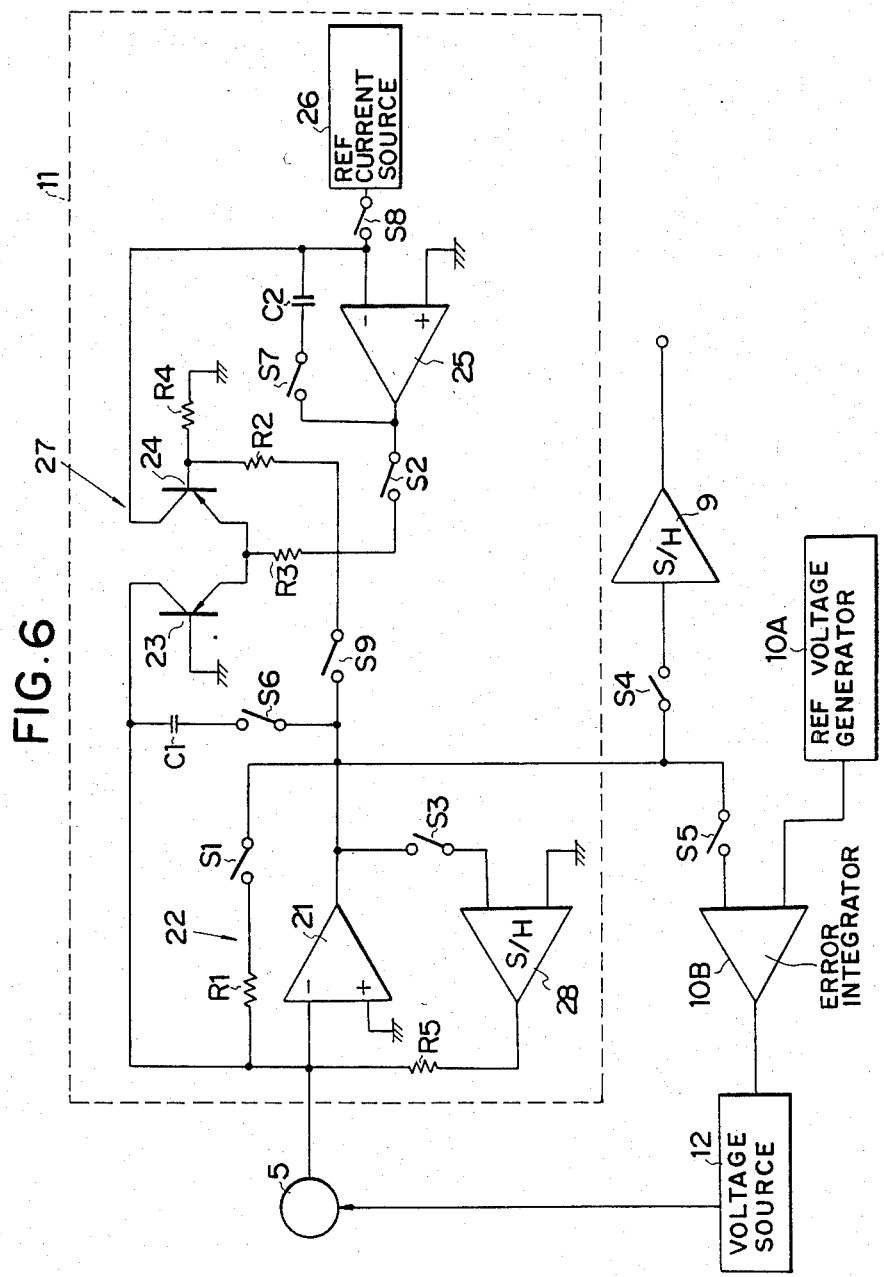
FIG. 6 is a circuit diagram, similar to FIG. 1, of an amplifier portion of another embodiment of the spectrophotometer.

FIG. 6 illustrates an essential portion of a further preferred embodiment of the spectrophotometer according to the invention. Like numerals designate like parts in both FIGS. 1 and 6.

In the circuit of FIG. 6, a series connection of a sixth switch S6 and a first capacitor C1 is inserted between the output terminal and the negative input terminal of the first operational amplifier 21 and parallel to the series connection of the first switch S1 and the resistor R1. Similarly, a series connection of a seventh switch S7 and a second capacitor C2 is inserted between the output terminal and the negative input terminal of the second operational amplifier 25. An eighth switch S8 is inserted between the reference current source 26 and a connection of the negative input terminal of the second operational amplifier 25 with the collector of the transistor 24. A ninth switch S9 is inserted between the output terminal of the first operational amplifier 21 and the base of the transistor 24 in series with the resistor R2. The organization of the remaining portion is the same as in the circuit of FIG. 1.

The newly added switches S6 to S9 in the circuit of FIG. 6 are driven by the above-mentioned first timing signal T1 and opened and closed at the same time and in the same manner as the second switch S2. That is, in the actual sample measurement, the switches S6 to S9 are closed in synchronism with the first timing signal T1 in the duration of a sample output impulse B and opened for the remaining period as the second switch S2 is. The operation of the remaining switches S1 to S5 is the same as in the circuit of FIG. 1.

In the sample measurement stage, opening of the switch S1 and closing of the switches S2 and S9 in the duration of a sample output impulse B renders the logarithmic amplifier 27 operative. For the purpose of rendering the logarithmic amplifier 27 operative, the switch S9 may be omitted or kept closed. In the period other than logarightmic amplification durations, however, opening of the switch S9 prevents current from flowing into the transistor 24, eventually eliminating any deleterious effect on current-voltage conversion by leak current from the transistors 23 and 24.

The capacitor C1 functions to accumulate electric charge after closing of the switch S6 in a logarithmic amplification duration, store the output voltage of the first operational amplifier 21 for a period from the end of the logarithmic amplification duration to the start of the subsequent logarithmic amplification duration, and apply the output voltage of the operational amplifier 21 corresponding to the preceding logarithmic amplification duration to the transistor 24 at the start of the subsequent logarithmic amplification duration. Such function of the capacitor C1 and switch S6 is effective particularly when a sample material to be analyzed has a reduced transmittance or increased radiation absorption, that is, the photomultiplier 5 produces output current of a reduced magnitude. The response of the operational amplifier 21 to the small output current of the photomultiplier 5 is delayed. It thus takes a substantial time until the output of the logarithmic amplifier 27 reaches a logarithmic value precisely corresponding to the output current of the photomultiplier 5, although the logarithmic amplification duration determined by the timing signal T1 is very short in fact. When the output current of the photomultiplier 5 is of a small magnitude, the absence of the capacitor C1 causes the logarithmic amplification duration to expire before a correct logarithmic output is created, failing to provide a correct value. A correct logarithmic value is readily reached by causing the capacitor C1 to store the output voltage of the operational amplifier 21 at the end of the preceding logarithmic amplification duration and starting from the stored voltage in the subsequent logarithmic amplification duration to compensate for a delay in the response of the operational amplifier 21. Of course, the compensation by the capacitor C1 is enabled only when a plurality of logarithmic amplification durations are repeated at each wavelength.

The second capacitor C2 has the same function as the first capacitor C1. However, the function of the second capacitor C2 is not so significant as the first capacitor C2 because the output current of the reference current source 26 applied to the operational amplifier 25 is always fixed. Therefore, the elimination of the second capacitor C2 and seventh switch S7 gives rise to no substantial problem in most practices. The eighth switch S8 is needed when the second capacitor C2 is provided. Opening of the switch S8 prevents the voltage charged in the second capacitor C2 from being applied to the transistor 24 in the period other than logarithmic amplification durations, eliminating any deleterious effect on current-voltage conversion and amplification by leak current from the transistors 23 and 24.

As apparent from the foregoing description, the feature of the present invention relating to a spectrophotometer of double beam type resides in that a current-voltage converting amplifier and a logarithmic amplifier in parallel connection are connected to the output terminal of the photo detector, and selection is made in synchronism with the operation of the beam path switching means between at least two states, a first state where a detector output is directly fed to the logarithmic amplifier without passing the current-voltage converting amplifier and a second state where a detector output is directly fed to the current-voltage converting amplifier without passing the logarithmic amplifier.

In the spectrophotometer of the invention, when it is desired to provide a logarithmic representation of analytical data, a sample output is directly logarithmically amplified without undergoing current-voltage conversion whereas reference and background outputs are only current-voltage converted and amplified without undergoing logarithmic amplification. In reading out sample measurement data, the elimination of undesirable factors such as noise, drift and offset in a stage preceding logarithmic amplification minimizes the influence of circuit noise on measured data, not only enabling to provide a correct transmittance value even when the intensity of a beam which has transmitted through a sample material is low, but also ensuring high precision measurement because of the minimized influence of noise on linearity of logarithmic values. In general, logarithmic amplifiers of current input type have a significantly wider dynamic range than those of voltage input type. The spectrophotometer of the invention allows an output current of the detector responding to a sample beam to be directly fed to the logarithmic amplifier without conversion into a voltage and prevents the detector output responding to the sample beam from being saturated in a circuit preceding the logarithmic amplifier, thereby expanding the dynamic range of the entire system over the prior art and ensuring more highly precise measurement. The spectrophotometer of the invention has another advantage that measured data may be represented in logarithm without logarithmically converting outputs of the detector which responds to a reference beam and background radiation, because the linearity of outputs of the detector responding to referene beams is otherwise lost so that processing such as correction of the detector outputs responding to reference beams and the reference voltage becomes complicated or processing of background radiation becomes complicated.

In the preferred embodiment wherein selection is made between two states, a first state where measured data is read out after logarithmic conversion and a second state where measured data is read out without logarithmic conversion, and logarithmically converted outputs and as-detected outputs (percentage representation) may be compared with each other for confirmation so that the reliability of logarithmically converted output data is further increased.

What we claim is:

1. In a spectrophotometer of the type comprising a radiation source, a reference cell, a sample cell, a radiation detector which produces an electrical output, and beam path switching means for directing monochromatic radiation of varying wavelengths from the source alternately to the reference and sample cells to form reference and sample beams and directing in synchronism the reference and sample beams to said detector, wherein an output of said detector which responds to the reference beam is fed back to said detector such that said output may be equal to a reference voltage upon measurement of a sample material in said sample cell at all wavelengths, whereby an output of said detector which responds to the sample beam represents the transmittance of the sample for each wavelength, the improvement comprising a current-voltage converting amplifier connected to the output terminal of said detector, a logarithmic amplifier connected to the output terminal of said detector, and synchronization switching means for alternately rendering said current-voltage converting amplifier and said logarithmic amplifier operative in synchronism with the operation of said beam path switching means, whereby selection is made by means of said synchronization switching means in synchronism with the operation of said beam path switching means between at least two states, a first state where an output of said detector is directly fed to said logarithmic amplifier without passing said current-voltage converting amplifier and a second state where an output of said detector is directly fed to said current-voltage converting amplifier without passing the logarithmic amplifier.

2. The spectrophotometer as set forth in claim 1 wherein said synchronization switching means is designed such that the reference output of said detector is directly amplified by said current-voltage converting amplifier in the duration when said detector responds to the reference beam to produce a reference output, and the sample output of said detector is directly amplified by said logarithmic amplifier in the duration when said detector responds to the sample beam to produce a sample output.

3. The spectrophotometer as set forth in claim 1 wherein said synchronization switching means includes a sync signal generator for generating at least one timing signal in response to switching of said beam path switching means, at least one first switch means for turning on and off said current-voltage converting amplifier in response to said timing signal, and at least one second switch means for turning on and off said logarithmic amplifier in response to said timing signal.

4. The spectrophotometer as set forth in claim 3 wherein said first switch means is opened and said second switch means is closed only when said timing signal is present, and said first switch means is closed and said second switch means is opened in the remaining period.

5. The spectrophotometer as set forth in claim 1 wherein said current-voltage converting amplifier comprises an amplifier connected to said detector and first feedback means connected across the amplifier for causing the amplifier to operate for current-voltage converting amplification, and said logarithmic amplifier comprises the common amplifier and second feedback means connected across the amplifier for causing the amplifier to operate for logarithmic amplification.

6. The spectrophotometer as set forth in claim 5 wherein said first feedback means includes a resistor connected across the amplifier, and said synchronization switching means includes a switch connected in series with the resistor.

7. The spectrophotometer as set forth in claim 5 wherein said second feedback means includes a resistor, a pair of transistors having commonly connected emitters and another amplifier, the components being connected for logarithmic amplification, and said synchronization switching means includes a switch connected in said second feedback means.

* * * * *